United States Patent [19]
Kokubo et al.

[11] Patent Number: 5,145,520
[45] Date of Patent: Sep. 8, 1992

[54] BIOACTIVE CEMENT

[75] Inventors: Tadashi Kokubo, Nagaokayo; Takao Yamamuro, Muko; Satoshi Yoshihara, Ohtsu, all of Japan

[73] Assignee: Kyoto University, Kyoto, Japan

[21] Appl. No.: 570,637

[22] Filed: Aug. 22, 1990

[30] Foreign Application Priority Data

Aug. 29, 1989 [JP] Japan ............... 1-220186

[51] Int. Cl.$^5$ ............ A61C 5/04; C09K 3/00
[52] U.S. Cl. ............... 106/35; 106/691; 106/690; 433/226; 433/228.1; 423/308; 423/309; 423/311; 423/312
[58] Field of Search ............ 106/35, 691, 690; 423/309, 312, 308, 311; 433/226, 228.1

[56] References Cited

U.S. PATENT DOCUMENTS

| | | | |
|---|---|---|---|
| Re. 33,161 | 2/1990 | Brown et al. | 106/690 |
| 4,271,057 | 6/1981 | Drake et al. | 501/48 |
| 4,591,384 | 5/1986 | Akahane et al. | 106/35 |
| 4,647,600 | 3/1987 | Kawahara et al. | 106/35 |
| 4,938,938 | 7/1990 | Ewers et al. | 423/308 |

FOREIGN PATENT DOCUMENTS

| | | |
|---|---|---|
| 0284074 | 9/1988 | European Pat. Off. |
| 60-36404 | 2/1985 | Japan |
| 60-61512 | 4/1985 | Japan |
| 61-236644 | 10/1986 | Japan |
| 62-12705 | 1/1987 | Japan |
| 62-72363 | 4/1987 | Japan |
| 62-83348 | 4/1987 | Japan |
| 62-153204 | 7/1987 | Japan |

OTHER PUBLICATIONS

"Bioactive Bone Cement Base on $CaO$—$SiO_2$—$P_2O_5$ Glass", J. Am. Chem. Soc. 74:pp. 1739–1741 (1991).

*Primary Examiner*—Mark L. Bell
*Assistant Examiner*—Melissa Bonner
*Attorney, Agent, or Firm*—Fleit, Jacobson, Cohn, Price, Holman & Stern

[57] ABSTRACT

An excellent bioactive cement is provided which can chemically and firmly bond to teeth or bones of living bodies, adapt the shape of defected portions of bones or teeth of living bodies, harden quickly, and exhibit high initial strength, without forming inflammation to the surrounding tissue of living bodies. The bioactive cement is composed of glass powder comprising Ca as a main constituent, and an aqueous solution of ammonium phosphate as a hardening liquid for the glass powder, and is economical and stable without loosing the fixation between the artificial biomaterial and the bones or teeth of living bodies nor degradation thereof in the living bodies during a long period of use in the living bodies.

7 Claims, No Drawings

BIOACTIVE CEMENT

BACKGROUND OF THE INVENTION

1. Field of the Invention

The present invention relates to bioactive cements used in medical and dental fields for bonding or fixing artificial biological materials, such as artificial bones or artificial teeth roots, etc., and which are also used as prosthetic materials for repairing defected portions of teeth or bones of living bodies.

2. Related Art Statement

Heretofore, in the fields of orthopedic surgery and dental surgery, when a portion of a bone is defected or cut away for the sake of bone fracture or bone tumor, etc., or when the bone of jaw is defected due to Riggs' disease or pulling out of a tooth, artificial biomaterials selected from metals, ceramics and crystalline glasses, etc., have been used to repair or remedy such defected portion.

Such artificial biomaterials are requested to adapt the shape of defected portion, and are desired quickly embedded and fixed in the defected portion. For that purpose, the defected portion has to be ground to meet the shape of the artificial biomaterial, otherwise the artificial biomaterial has to be worked to meet the shape of the defected portion. However, such grinding or working is quite difficult to perform precisely.

Therefore, when using the artificial biomaterials in living bodies, some cements have been used, in order to bond and fix the artificial biomaterials to bones or teeth of living bodies. For example, in the field of orthopedic surgery, cements made of PMMA (polymethylmethacrylate) has been widely used. In the field of dental surgery, cements made of zinc phosphate or carboxylate have been used. Moreover, granules of apatite or alumina ceramics have been directly filled in the defected portion so as to adapt the shape of the defected portion.

However, though the above-described various cements can firmly bond to the artificial biomaterials, they can not chemically bond to bones of living bodies. Thus, if the cement is used in the defected portion for a long period of time, the fixation between tooth or bone of living body and the cement is likely loosened. Moreover, granules of apatite or alumina ceramics do not bond with each other, so that they have to be fixed in the defected portion with the aid of the cement.

Recently, in consideration of the above situations, various bioactive cements have been reported which can chemically bond to bones of living bodies. This type of bioactive cements use crystalline powders of calcium phosphate, etc., alone or in admixture, which is/are reacted with a hardening liquid to precipitate crystals of hydroxyapatite, etc. The bioactive cements are classified into two types depending on the type of the hardening liquid. One type of bioactive cements is those that use an aqueous solution of citric acid or malic acid, etc., as the hardening liquid, and the other type of bioactive cements are those that use water as the hardening liquid. The former type of cements harden in a short time and exhibit high initial strength, so that quick and strong bonding and fixing of the artificial biomaterials by the cements can be expected. However, due to the use of the aqueous solution of the organic acid, they are, when used, likely to incur an inflammatory reaction to the surrounding tissue of living bodies, and has a problem in that the cements are likely deteriorated in living bodies due to their high degradation rate. Meanwhile, the latter type of cements do not use an organic acid, so that they do not incur an inflammatory reaction to the surrounding tissue of living bodies, however, they have slow hardening speed and hence low initial strength and can not attain practically necessary quick bonding and fixing of the artificial biomaterials to bones or teeth of living bodies.

SUMMARY OF THE INVENTION

An object of the present invention is to provide a bioactive cement which can quickly set and harden by itself to fix and bond the artificial biomaterial well without incurring an inflammatory reaction to the surrounding tissue of living bodies, and which can chemically and stably bond with bones or teeth of living bodies for a long period of time.

The bioactive cement of the present invention is composed of glass powder comprising Ca as a constituent, and an aqueous solution of ammonium phosphate as a hardening liquid for the glass powder.

In using the bioactive cement of the present invention, the glass powder and the aqueous solution are mixed thoroughly before the use and served for use.

Preferably, the amount of Ca in the glass powder is 20-60 wt % calculated as CaO.

The glass powder according to the present invention is preferably small in diameter since the powder of smaller diameter gives higher strength of cement. Preferably, glass powder of a diameter of not over than 44 $\mu$m is used.

In order to increase the strength of the hardened cement, the concentration of the phosphate ions in the aqueous solution of the ammonium phosphate which is used as the hardening liquid, is preferably as high as possible. Use of orthophosphoric acid is not desirable, because the hardening liquid is caused to acidic by the use of the orthophosphoric acid. The hardening liquid is made substantially neutral of a pH of 6.0-8.5 by the use of ammonium dihydrogen phosphate or diammonium hydrogen phosphate as the source of phosphoric acid. Such neutralization allows the hardening liquid to prevent inflammation of the surrounding tissue of living bodies from occurring.

In the present invention, glass powder comprising Ca as a essential constituent is mixed with the aqueous solution of ammonium phosphate to dissolve out $Ca^{2+}$ ions from the surface of the glass powder. The $Ca^{2+}$ ions dissolved out from the glass powder and existing on the surface of the glass powder react with $HPO_4^{2-}$ (phosphoric acid) ions in the hardening liquid comprising ammonium phosphate as a essential component to form precursors, such as, amorphous calcium phosphate, calcium secondary hydrogen phosphate dihydrate ($CaHPO_4 \cdot 2H_2O$) and ammonium calcium phosphate hydrate ($CaNH_4PO_4 \cdot H_2O$), etc., and further hydroxyapatite which allows hardening of the cement. Hydroxyapatite has a superior chemical reactivity with teeth or bones in living bodies and becomes a stable substance in living bodies.

Glass powders have different $Ca^{2+}$ ions dissolution speed depending on their compositions, and different hardening time depending on the concentration of $HPO_4^{2-}$ ions in the hardening liquid in view of the composition of the glass powder. A glass powder having an appropriate $Ca^{2+}$ ions dissolution speed is selected and used depending on the necessity of use.

DESCRIPTION OF THE PREFERRED EMBODIMENTS

Hereinafter, the present invention will be explained in more detail with reference to Examples.

EXAMPLES 1-8

Table 1 below shows embodiments and referential examples of the present invention.

Glass powders are reciped so as to obtain glass powders of Example 1 and Referential Example 1 of a composition consisting in weight basis of 46.5% of CaO, 36.0% of $SiO_2$, 17.0% of $P_2O_5$ and 0.5% of $CaF_2$, a glass powder of Example 2 of a composition consisting in weight basis of 41.0% of CaO, 37.5% of $SiO_2$, 16.0% of $P_2O_5$, 5.0% of MgO and 0.5% of $CaF_2$, a glass powder of Example 3 of a composition consisting in weight basis of 49.0% of CaO, 31.0% of $SiO_2$, 15.0% of $P_2O_5$ and 5.0% of $Na_2O$, a glass powder of Example 4 of a composition consisting in weight basis of 45.5% of CaO and 54.5% of $SiO_2$, and a glass powder of Example 5 of a composition consisting in weight basis of 26.5% of $Na_2O$, 26.5% of CaO and 47.0% of $SiO_2$. The reciped powders of glass are melted and vitrified at 1,450°–1,650° C. for 2 hours, then shaped on rollers, ground in a ball mill, and separated or sieved to obtain glass powders of a fineness of $-330$ meshes.

The powders of Referential Examples 2 and 3 are prepared by synthesizing α-tricalcium phosphate by dry process, grinding, and separating the ground to $-330$ mesh similarly as in the cases of the glass powders of the other Examples.

The hardening liquids of Examples 1–5 are prepared by dissolving appropriate amounts of diammonium hydrogen phosphate and/or ammonium dihydrogen phosphate in water so as to adjust the pH of the solution to 7.4 (20° C.). Pure water is used in Referential Examples 2 and 3, and an aqueous solution of 1% citric acid is used in Referential Example 3, as the hardening liquid.

The ratio of the amount of the hardening liquid to the amount of the powder, which is the so-called powder liquid ratio, is selected within a range of 0.35–0.65 mλ of the hardening liquid per 1 g of the powder, and the value of the powder liquid ratio which gives the largest value of compression strength is selected and determined as the representative value of the powder liquid ratio.

Characteristic properties of the cements are evaluated by initial strength of the cements and reaction to the surrounding tissue of the living body.

The initial strengths of the cements are measured according to JIS T 6602 which defines a method of determining a strength of dental zinc phosphate cement. At first, the powder and the hardening liquid are thoroughly blended, then cast into a desired mold, and hardened for 1 hour. Thereafter, the cast materials are taken out from the mold, immersed in a simulation fluid which simulates human body fluid for 24 hours, and then measured on wet compressive strength. The wet compression strength is evaluated as the initial strength of the cement. The strength of the cement of the present invention increases with the time of the immersion in the simulation fluid. For example, the cement of Example 1 has a compressive strength of 80 MPa after immersion of 7 days in the simulation fluid.

Also, a hole of 4 mmφ is bored on the proximal tibial metaphysis of rats and filled with the blended bioactive cement of respective Example. The rats are killed after 4 weeks and the tissues around the cement are extracted to examine presence or non-presence of inflammation and the bonding strengths of the cement to the bone around the cement.

TABLE 1

|  | Example 1 | Example 2 | Example 3 | Example 4 | Example 5 | Reference Example 1 | Reference Example 2 | Reference Example 3 |
|---|---|---|---|---|---|---|---|---|
| Powder | glass | glass | glass | glass | glass | glass | α-tricalcium phosphate | α-tricalcium phosphate |
| Hardening liquid | aqueous solution of ammonium phosphate | aqueous solution of ammonium phosphate | aqueous solution of ammonium phosphate | aqueous solution of ammonium phosphate | aqueous solution of ammonium phosphate | water | water | aqueous solution of citric acid |
| Powder liquid ratio (g/ml) | 1/0.5 | 1/0.5 | 1/0.55 | 1/0.55 | 1/0.6 | 1/0.5 | 1/0.45 | 1/0.6 |
| Compressive strength (MPa) | 60 | 30 | 50 | 30 | 30 | 12 | 8 | 80 |
| Inflammation | none | none | none | none | none | none | none | yes |
| Bonding to bone of living body | yes | yes | yes | yes | yes | yes | yes | yes |

As explained in detail in the foregoings, the bioactive cement of the present invention quickly and firmly bonds artificial biomaterials to teeth or bones of living bodies without incurring inflammation to the surrounding tissue of living bodies. Furthermore, it chemically bonds to teeth or bones of living bodies, so that the fixation of artificial biomaterials to the bones or teeth is not loosened during a long period of use. Therefore, it is very effective in fixing artificial bones or artificial teeth roots to bones of living bodies, and also quite effective as a prosthetic material for repairing various shapes of defected portion of bones or teeth of living bodies.

Although the present invention has been explained with specific examples and numerical values, it is of course apparent to those skilled in the art that various changes and modifications thereof are possible without departing from the broad spirit and aspect of the present invention as defined in the appended claims.

We claim:

1. A bioactive cement, consisting of glass powder having CaO and $SiO_2$ as essential constituents; and an aqueous solution of ammonium phosphate as a hardening liquid for the glass powder.

2. The bioactive cement as defined in claim 1, wherein the glass powders have diameters of not over than 44 μm.

3. The bioactive cement as defined in claim 1, wherein the ammonium phosphate is selected from the group consisting of ammonium dihydrogen phosphate and diammonium hydrogen phosphate.

4. The bioactive cement as defined in claim 1, wherein the ratio of the amount of the hardening liquid to the amount of the glass powder is within a range of 0.35–0.65 mλ of the hardening liquid per 1 g of the glass powder.

5. The bioactive cement as defined in claim 1, wherein the hardening liquid has a pH of 6.0–8.5.

6. The bioactive cement as defined in claim 1, wherein the amount of CaO in the glass powder is 20–60 wt %.

7. The bioactive cement as defined in claim 1, wherein the amount of $SiO_2$ in the glass powder is 31.0–54.5 wt %.

* * * * *